United States Patent [19]

Cordi

[11] Patent Number: 5,187,171
[45] Date of Patent: Feb. 16, 1993

[54] USE OF A GLYCINE B PARTIAL AGONIST AS AN ANTIPSYCHOTIC

[75] Inventor: Alex A. Cordi, St. Louis, Mo.

[73] Assignee: G. D. Searle & Co., Chicago, Ill.

[21] Appl. No.: 294,851

[22] Filed: Jan. 9, 1989

[51] Int. Cl.$^5$ .................... A61K 31/41; A61K 31/42
[52] U.S. Cl. ..................................... 514/359; 514/378
[58] Field of Search ................................ 514/378, 359

[56] References Cited

PUBLICATIONS

C. V. Showalter et al., *Amer. J. Psychiat.*, 134, 1234 (1977).
S. H. Snyder, *Nature*, 285, 355–356 (1980).
P. Loo et al., *Eur. J. Pharmacol*, 123, 467–468 (1986).
C. A. Tamminga et al., *Synapse*, 1, 497–504 (1987).
R. Quirion et al, *Peptides*, 5, 967–973 (1984).
O. Mayer et al, *Arzneim. Forsch.*, 21 (2), 298–303 (1971).
M. Vojtechovsky, *Act. Nerv. Super.*, 7(3), 269 (1965).
V. Vitek et al, *Psychopharmacologia*, 7(3), 203–219 (1965).
G. E. Crane, *Comp. Psychiat.*, 2, 51–53 (1961).
J. Simeon et al., *Compri, Psychiat.*, 11, 80–88 (1970).
Martindale, The Extra Pharmacopoeia, p. 1152 28th Ed (1982).

*Primary Examiner*—S. J. Friedman
*Attorney, Agent, or Firm*—J. Timothy Keane; Paul D. Matukaitis

[57] ABSTRACT

A class of Glycine B partial agonists is described for use for treatment of psychosis. Preferred Glycine B partial agonists include amino-isoxazolidone compounds such as D-cycloserine and its prodrugs.

8 Claims, 2 Drawing Sheets

USE OF A GLYCINE B PARTIAL AGONIST AS AN ANTIPSYCHOTIC

FIELD OF THE INVENTION

This invention is in the field of clinical neurology and relates specifically to compounds, formulations and methods for treatment of psychotic disorders.

BACKGROUND OF THE INVENTION

There are many psychotic states for which therapeutic treatments are under investigation. Drugs which are currently available on the market are thought to act as antagonists at the dopaminergic receptors located in the Central Nervous System (CNS), examples of such drugs being haloperidol and chlorpromazine. These drugs typically induce long lasting and sometimes irreversible side-effects, si. ardive dyskinesia. Thus, the search for improvements in therapy for psychotic disorders has been directed to use of drugs with a different mode of action.

Phencyclidine [1-(-phenylcyclohexyl)piperidine; PCP] is a known general anesthetic and is in use as an animal tranquilizer. PCP is a potent psychotomimetic agent used frequently as a "street" drug. Widespread abuse of PCP has led to increased incidence of PCP-induced psychoses [C. V. Showalter et al, Amer. J Psychiat., 134, 1234 (1977)]. PCP abusers experience an apparent sensory isolation accompanied by a feeling of depersonalization which can be terrifying to the person. These subjective changes make PCP an appropriate drug model for study of schizophrenia. The most impressive evidence that PCP psychosis resembles schizophrenia is the fact that drug users have been mistaken by experienced psychiatrists for schizophrenics before obtaining the history of drug use [S. H. Snyder, Nature, 285, 355-356 (1980)].

PCP has been reported to modulate allosterically the NMDA receptor [P. Loo et al, Eur. J. Pharmacol., 123, 467-468 (1986)] and it has been speculated that the psychotomimetic activity of PCP is related to its antagonism of NMDA transmission [C. A. Tamminga et al, Synapse, 1, 497-504 (1987)]. Facilitation of NMDA transmission by action at the glycine modulatory site may antagonize the effect of an endogenous PCP-like ligand [R. Quirion et al, Peptides, 5, 967-973 (1984)].

Amino-oxazolidone compounds have been investigated for CNS effects. For example, the compound D-cycloserine, in its D- and L-isomer forms, has been evaluated for CNS effects in animals [O. Mayer et al, Arzneim. Forsch., 21(2), 298-303 (1971)]. These cycloserine isomers have also been evaluated for psychological and physiological effects in human subjects. For example, D-cycloserine when administered at 500 mg/day doses to healthy human subjects, appeared to stimulate slight sociability, but with depressed mental alertness [M. Vojtechovsky, Act. Nerv. Super., 7(3), 269 (1965)]. Also, D-cyloserine has been administered at 1000 to 1500 mg/day to healthy volunteers whose blood levels showed increased levels of monoamine oxidase enzyme activity [V. Vitek et al, Psychopharmacologia, 7(3), 203-219 (1965)].

D-cycloserine has been investigated as a therapeutic agent for mental disorders in clinical trials, wherein D-cycloserine was administered to mentally disturbed patients at doses of 500 mg. per day [G. E. Crane, Compr. Psychiat., 2, 51-53 (1961)]. In such clinical trials, improvements in depression, insomnia, anexoria or tension were found for some patients, while patients suffering from severe neurosis or psychosis responded poorly to such medication. Moreover, D-cycloserine has been used to exacerbate the symptoms of schizophrenia in an attempt to cure the ailment by symptom provocation [J. Simeon et al, Compr. Psychiat., 11, 80-88, (1970)].

It appears that D-cycloserine, at the dose levels used in these studies, is acting as an antagonist at the glycine site of the NMDA-PCP receptor- complex mimicking the action of PCP by inducing psychosis.

DESCRIPTION OF THE INVENTION

Figure 1:
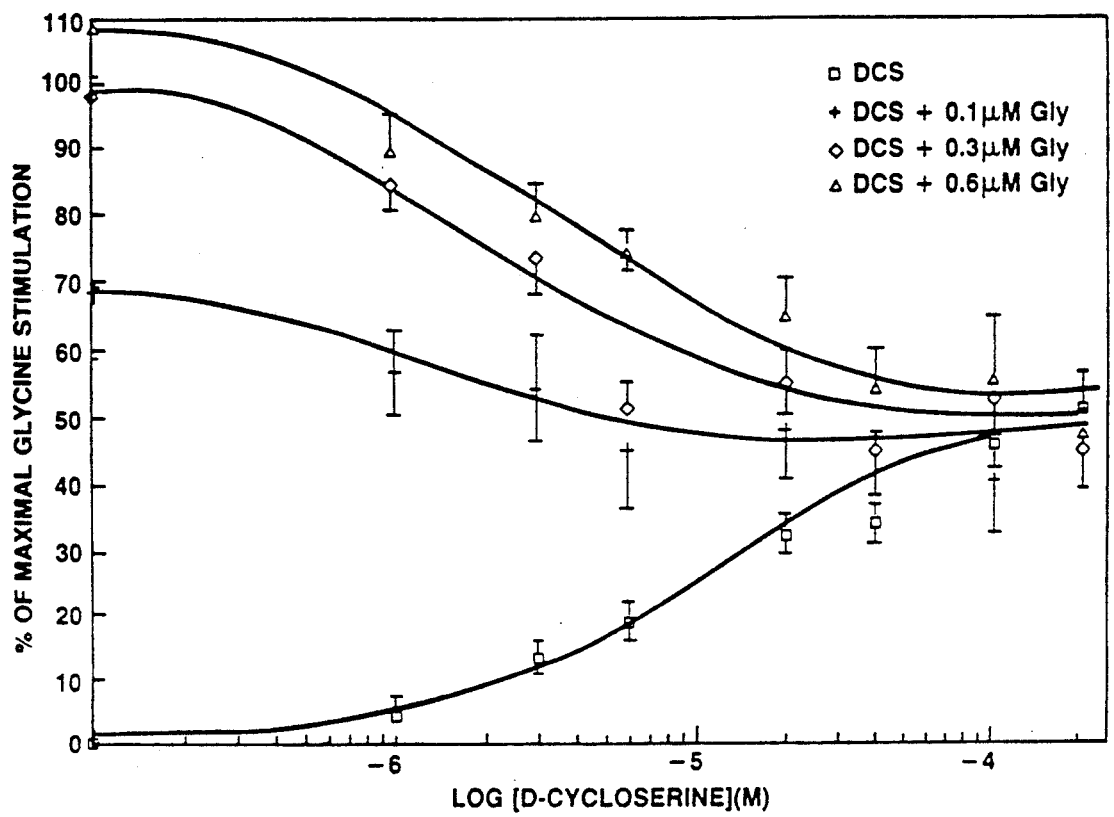
FIG. 1 is a graph showing concentration of D-cycloserine influence on maximal glycine stimulation of TCP binding in the presence of various concentrations of glycine.

Treatment of a psychotic disorder is achieved by treatment of a subject, susceptible to or suffering from a psychotic disorder, with a therapeutically-effective amount of a Glycine B partial agonist or a prodrug thereof. Such Glycine B partial agonist may be provided by one or more amino-isoxazolidone compounds selected from the family of compounds of Formula I:

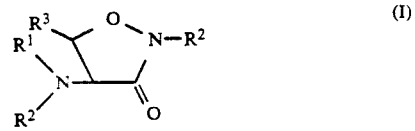

wherein $R^1$ is selected from hydrido, alkyl, haloalkyl, alkoxyalkyl, cycloalkyl, aralkyl and aryl; wherein $R^2$ is selected from hydrido, alkyl, aralkyl, aryl,

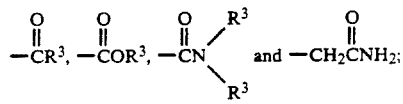

wherein $R^1$ and $R^2$ may be taken together to form a Schiff-base derived group selected from derivatives of aldehydes and ketones; wherein $R^3$ is selected from hydrido, alkyl, haloalkyl, alkoxy, alkoxyalkyl, cycloalkyl, aralkyl and aryl; or a pharmaceutically-acceptable salt thereof. Where compounds of Formula I exist as optical isomers, the D-configuration is generally preferred.

It is believed that a psychotic disorder is linked to an increased concentration of an endogenous ligand acting at the PCP site of the NMDA-PCP receptor complex. This endogenous ligand is believed to be PCP-like in character in that interaction of the ligand with the NMDA-PCP receptor complex results in inhibition of the opening of the ion channel triggered by NMDA. A Glycine B agonist compound of the invention, by potentiating NMDA transmission, will thus antagonize the effect of the endogenous ligand. Inasmuch as the endogenous ligand is responsible for psychotic disorders, such as schizophrenia, the blocking of such ligand action should result in reduction of psychotic behavior. In particular, it is believed that the compounds of the invention will be useful in the treatment of acute or chronic PCP-induced psychosis.

A preferred family of compounds consists of compounds wherein $R^1$ is selected from hydrido, lower alkyl, haloalkyl, cycloalkyl, alkoxyalkyl, phenalkyl and phenyl; wherein $R^2$ is selected from hydrido, lower alkyl, phenalkyl, phenyl,

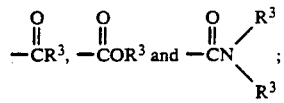

wherein the Schiff-base derived group is derived from acetylacetone, salicylaldehyde, benzophenone derivatives and acetylacetic acid esters; and wherein $R^3$ is selected from hydrido, lower alkyl and benzyl.

A more preferred group of compounds within Formula I consists of these compounds wherein $R^1$ is hydrido; wherein $R^2$ is selected from

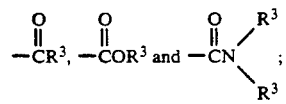

wherein the Schiff-base derived group is selected from

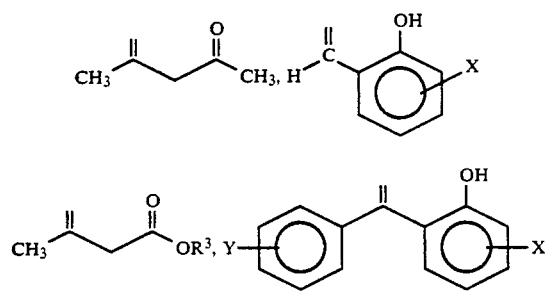

wherein each of X and Y is independently one or more groups selected from hydrido, lower alkyl and halo; and wherein $R^3$ is selected from hydrido, lower alkyl and phenyl.

A most preferred group of compounds within Formula I consists of those compounds wherein $R^1$ is selected from hydrido and the Schiff-base derived groups

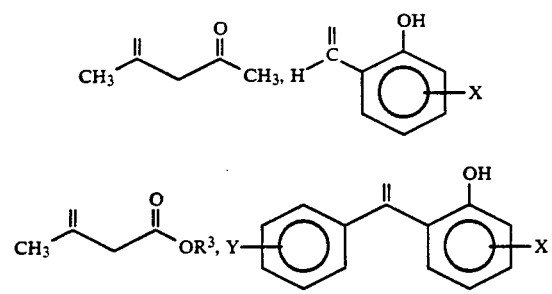

wherein each of X and Y is independently selected from fluoro, chloro and bromo; and wherein each of $R^2$ and $R^3$ is hydrido.

A most preferred specific compound of Formula I is the compound 4-amino-3-isoxazolidone having the structural formula

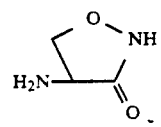

This compound exists in the L- and D-isomeric forms, of which the compound D-cycloserine is most highly preferred.

Also embraced by Formula I are the tautomeric forms of these compounds as represented by Formula II:

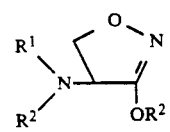

wherein $R^1$, $R^2$ and $R^3$ are as defined for the compounds of Formula I.

The term "hydrido" denotes a single hydrogen atom (H) which may be attached, for example, to a carbon atom or attached to an oxygen atom to form an hydroxyl group. Where the term "alkyl" is used, either alone or within another term such as "haloalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about ten ring carbon atoms, and preferably having three to about five carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkoxy" and "alkoxyalkyl" embrace linear or branched oxy-containing radicals having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "aralkyl" is exemplified by "phenalkyl" of which benzyl is a specific example.

Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl.

Included within the family of compounds of Formulas I and II are the isomeric forms of the described compounds including diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I and II contain basic nitrogen atoms, such salts are typically acid addition salts or quaternary salts. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I and II.

The term "prodrug", as used herein, embraces compounds which are precursors of Glycine B partial agonists. Such precursor compounds can release the Glycine B partial agonist by some chemical or enzymatic reaction taking place in the body or, optimally, in the brain.

Compounds of Formula I and Formula II can be synthesized by methods described in the literature. For example, syntheses of N-acyl derivatives and Schiff-base derivatives of D-cycloserine are described by N. P. Jensen et al, *J. Med. Chem.*, 23 6-8 (1980). Syntheses of N,N'-diacyl derivatives of cycloserine are described by J. C. Howard, *J. Org. Chem.*, 46, 1720-1723 (1981). Syntheses of alkyl derivatives of cycloserine are described by C. H. Stammer, *J. Med. Chem.*, 13(6), 1013 (1970). Syntheses L- and D-isomers of cycloserine, as well as analogues thereof, are described by Pl. A. Plattner et al, *Helv Chim. Acta.*, 40, 1531 (1957).

BIOLOGICAL EVALUATION

Glycine Binding Assay Procedure

Synaptic plasma membranes (SPM) were prepared from rat forebrain and stored as previously described [J. B. Monahan and J. Michel, *J. Neurochem.*, 48, 1699-1708 (1987)]. Frozen membranes were thawed and diluted 1:20 with 0.04% triton X-100 in 50 mM tris/acetate (pH 7.4). Following incubation at 37° C. for 30 min., the SPM were collected by centrifugation at 95,000 × g for 15 min. The pellet was resuspended in 50 mM tris/acetate (pH 7.4, triton-free) and hand-homogenized five times. The membranes were again centrifuged as above. The pellet was washed two additional times with 50 mM tris/acetate (without homogenization) and centrifuged. The final pellet was resuspended with homogenization in 50 mM tris/acetate.

In the general receptor binding assay procedure, 10 nM [$^3$H]glycine was added to the appropriate concentration of the test compounds and the assay initiated by the addition of 0.2-0.4 mg of ice cold SPM. The assay, which was done in 1.5 ml centrifuge tubes, was adjusted to a total volume of 1.0 ml with all additions being made in 50 mM tris/acetate, pH 7.4 at 4° C. After a 10 minute incubation at 2° C., the samples were centrifuged for 15 min. at 12,000 g (4° C.) in a Beckman Microfuge 12. The supernatant was aspirated and the tube tip containing the pelleted membranes cut off and agitated in 0.5 ml of Beckman BTS-450 tissue solubilizer for a minimum of 6 hours at room temperature. Beckman MP scintillation cocktail (5 ml) containing 7 ml/liter acetic acid was then added and the samples counted on a Beckman LS 5800 liquid scintillation counter with automatic corrections for quenching and counting efficiency. Nonspecific binding was defined as the residual binding in the presence of 0.1 mM glycine and usually amounted to 25-35% of the total binding. The binding of [$^3$H]glycine to the SPM was analyzed using Scatchard and Hill transformations and the $K_i$ for other compounds was determined using logit-log analysis. Calculations and regression analysis were performed using templates developed for Lotus 123 as previously described.

| Result | $K_i$ (μM) |
| --- | --- |
| Glycine | 0.18 |
| D-cycloserine | 1.92 |
| L-cycloserine | >100 |

TCP Modulation Assay

[$^3$H]TCP binding was performed using Triton X-100 washed synaptic plasma membranes (SPM) prepared from rat forebrain (30-45 day old, male Sprague-Dawley; Sasco, St. Charles, Mo.) as described previously [J. W. Thomas, W. F. Hood, J. B. Monahan, P. C. Contreras and T. L. O'Donohue, *Brain Res.*, 442, 396-398 (1988)]. The assay was initiated by the addition of SPM (0.15-0.25 mg) to an incubation containing 2.0 nM [$^3$H]TCP (47.1 Ci/mmole; New England Nuclear, Boston, Mass.) and various concentrations of the appropriate test compound in a total volume of 0.5 ml (all additions were made in 5 mM Tris/HCl buffer, pH 7.4) and continued for 60 min; at 25° C. The samples were then filtered through glass fiber filters (Schleicher and Schuell #32) which were pretreated with 0.05% (v/v) polyethylenimine. The filters were washed and the radioactivity quantitated by liquid scintillation spectrometry. Stimulation of [$^3$H]TCP binding was measured as an increase in basal specific binding (basal binding=2583±381 DPM and this value increased to a maximum of 4712±779 DPM in the presence of 0.6 μM glycine) with nonspecific binding as the residual binding in the presence of 60 μM PCP (562±30 DPM). The $K_d$ for [$^3$H]TCP under basal conditions was 44 nM. The $EC_{50}$ values for the stimulation of [$^3$H]TCP binding were determined using a four parameter logistic regression analysis.

D-Cycloserine stimulates basal [$^3$H]TCP binding in a dose dependent manner with an $EC_{50}$=19.7 μM. Previous data show that D-cycloserine interacts with the NMDA-associated [$^3$H]glycine recognition site ($K_i$=2.33±0.29μM). No affinity for the NMDA recognition site, however, was detected as evidenced by the lack of displacement of NMDA-specific L-[$^3$H]glutamate binding ($K_i$>100 μM). This finding indicates that D-cycloserine enhances [$^3$H]TCP binding through its interaction with the NMDA receptor-associated glycine recognition site (herein defined as the "Glycine B receptor"). The maximal stimulation produced by D-cycloserine, however, was significantly less than that produced by both glycine and D-serine.

This apparent lower efficacy indicates the potential partial agonist character of D-cycloserine which was confirmed by the following experiment. As shown in FIG. 1, in the absence of exogenously added glycine, D-cycloserine has agonist properties and stimulates [$^3$H]TCP binding to a maximum of 40–50% of the stimulation induced by glycine alone. However, in the presence of various concentrations of glycine (0.1–0.6 μM), D-cycloserine has an apparent antagonist character and reduces the maximal level of glycine stimulation. These data provide a family of D-cycloserine dose-response curves (generated in the presence of several fixed concentrations of glycine) which asymptotically approach 40–50% of the maximal stimulation induced by glycine alone, a pattern characteristic of compounds with partial agonist properties as is known with different compounds acting on other receptors.

Figure 2:
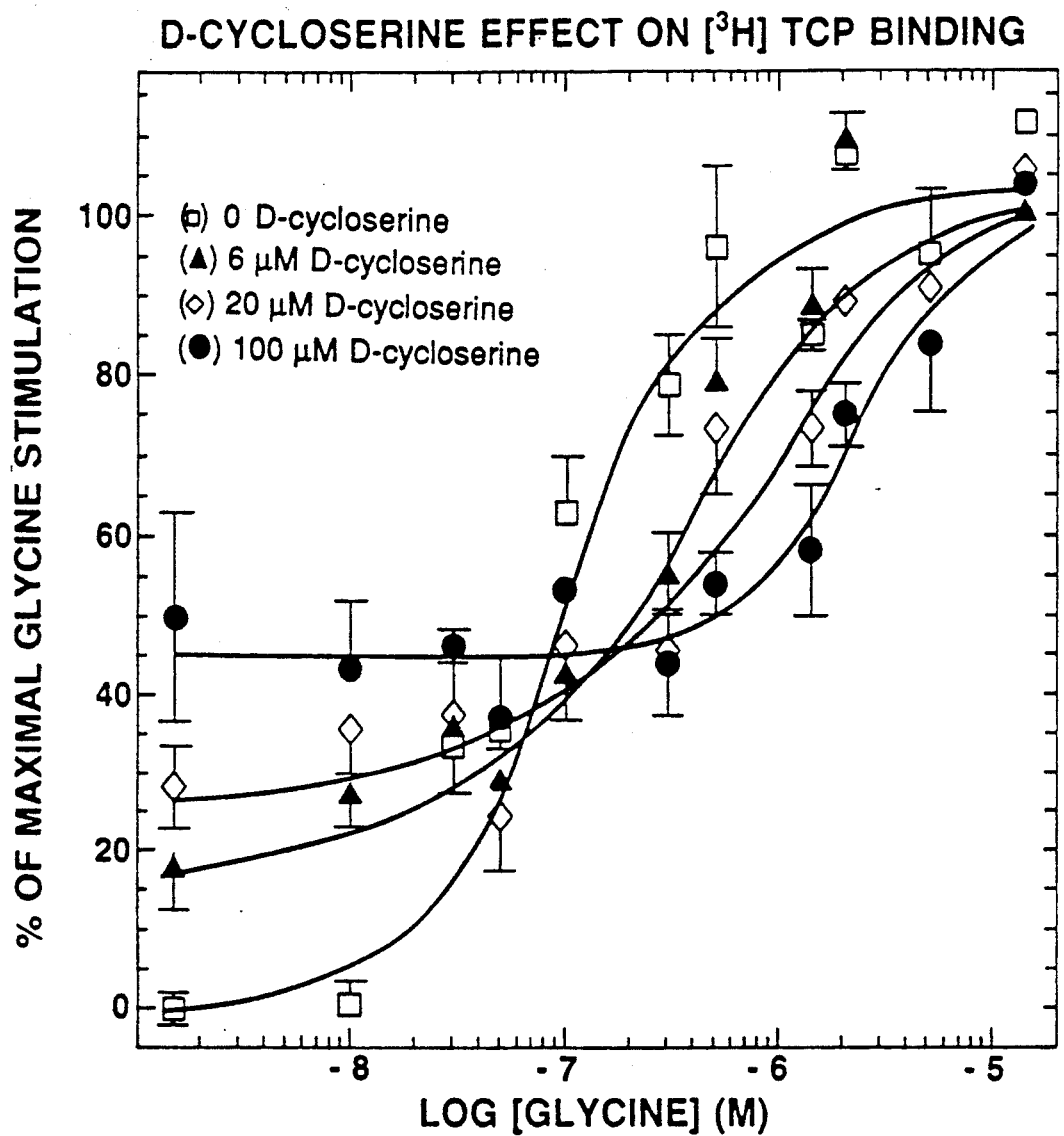
FIG. 2 is a graph showing concentration of glycine influence on maximal glycine stimulation of TCP binding in the presence of various concentrations of D-cycloserine.

Further confirmation of the partial agonist character of D-cycloserine was demonstrated in experiments wherein a glycine dose-response analysis was performed in the presence of several fixed concentrations of D-cycloserine (0–100 μM). As shown in FIG. 2, D-cycloserine potentiated the glycine stimulation of [$^3$H]TCP binding at glycine concentrations below 0.1 μM, while at higher glycine concentrations (0.1–15 μM) D-cycloserine produced a rightward shift in the dose-response curve. These results are again consistent with partial agonist characteristics.

The functional analysis of D-cycloserine described herein is the first report of a compound interacting at this glycine modulatory site exhibiting partial agonist characteristics. These results, along with the favorable brain bioavailability of the compound, are evidence for involvement of the NMDA/PCP receptor in psychosis treatment, and thus make D-cycloserine a valuable tool to probe NMDA receptor function.

The acidic amino acids, aspartic and glutamic acid, have been found to possess both excitatory and excitotoxic properties [J. W. Olney, *Science*, 164, 719–721 (1969); J. W. Olney et al., *Exp. Brain Res.*, 14, 61–76 (1971)]. Indeed, neurons which have excitatory amino acid receptors on their dendritic or somal surfaces undergo acute excitotoxic degeneration when these receptors are excessively activated by glutaric acid.

Glycine agonists which have a potentiating effect on the NMDA transmission would be expected to increase the glutamic acid excitotoxicity. A Glycine B partial agonist achieves beneficial excitatory effects without the detrimental excitotoxic side effect. Most glycine ligands are very polar molecules and hardly cross the blood brain barrier. Because of the difficulty in crossing the blood brain barrier, such ligands are not bioavailable at concentrations effective to be therapeutically beneficial. It is known that D-cycloserine easily passes the blood brain barrier [Goodman and Gilman, *The Pharmacologic Basis of Therapeutics*, Ch., 53, 1210–1211 (1980)].

It was surprising and unexpected that D-cycloserine was found to have such a good affinity for the strychnine-insensitive glycine receptor as shown by the binding data above. Glycine agonists are believed to facilitate NMDA transmission and, therefore, to have a potential for reversing the symptoms of schizophrenia and, in particular, to reverse the symptoms induced by acute or chronic PCP intoxication.

Administration of compounds within Formulas I and II to humans can be by any technique capable of introducing the compounds into the bloodstream of a human patient, including oral administration, and by intravenous, intramuscular and subcutaneous injections.

Compounds indicated for therapy will preferably be administered in a daily dose generally in a range, depending upon patient condition and symptomology, which is an amount therapeutically effective at the lowest possible dose up to about 1 mg per kilogram of body weight per day. A more preferred dosage will be a range from about 0.01 mg to about 1 mg per kilogram of body weight. Most preferred is a dosage in a range from about 0.05 to about 0.5 mg per kilogram of body weight per day. A suitable dose can be administered in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active agent or dispersing agent. Such capsules or tablets may contain a controlled-release formulation as may be provided by a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to treat a psychotic disorder by administering to a subject susceptible to or suffering from a psychotic disorder a therapeutically-effective amount of a Glycine B partial agonist or a prodrug thereof selected from the family of compounds of the formula

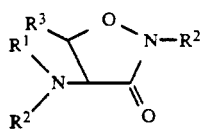

wherein R¹ is selected from hydrido, alkyl, haloalkyl, alkoxyalkyl, cycloalkyl, aralkyl and aryl; wherein R² is selected from hydrido, alkyl, aralkyl, aryl,

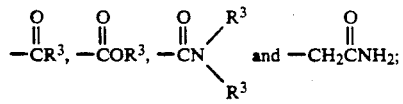

wherein R¹ and R² which are attached to the same nitrogen atom may be taken together to form a Schiff-base derived group selected from derivatives of aldehydes and ketones; wherein R³ is selected from hydrido, alkyl, haloalkyl, alkoxy, alkoxyalkyl, cycloalkyl, aralkyl and aryl; or a pharmaceutically-acceptable salt thereof.

2. The method of claim 1 wherein R¹ is selected from hydrido, lower alkyl, haloalkyl, cycloalkyl, alkoxyalkyl, phenalkyl and phenyl; wherein R² is selected from hydrido, lower alkyl, phenalkyl, phenyl,

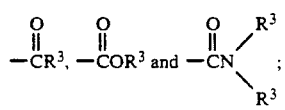

wherein the Schiff-base derived group is derived from acetylacetone, salicylaldehyde, benzophenone derivatives and acetylacetic acid esters; and wherein R³ is selected from hydrido, lower alkyl and benzyl.

3. The method of claim 2 wherein R¹ is hydrido; wherein R² is selected from

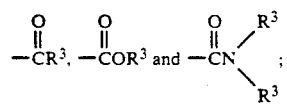

wherein the Schiff-base derived group is selected from

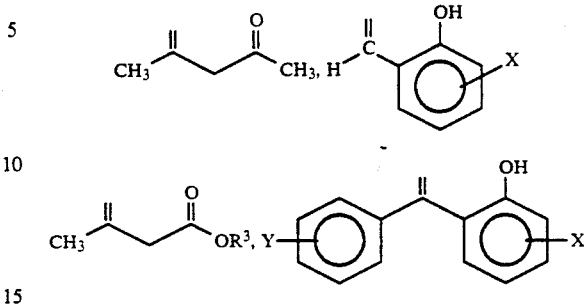

wherein each of X and Y is independently one or more groups selected from hydrido, lower alkyl and halo; and wherein R³ is selected from hydrido, lower alkyl and phenyl.

4. The method of claim 3 wherein R¹ is selected from hydrido and the Schiff-base derived groups

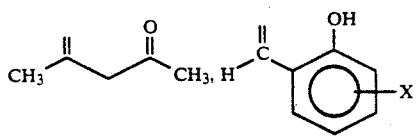

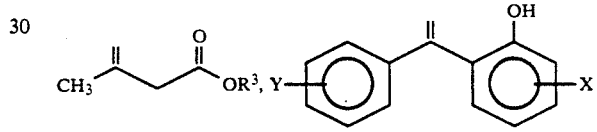

wherein each of X and Y is independently selected from fluoro, chloro and bromo; and wherein each of R² and R³ is hydrido.

5. The method of claim 4 said compound is D-4-amino-3-isoxazolidone.

6. The method of claim 1 wherein said compound is an optically-active isomer in the D-configuration.

7. The method of claim 1 wherein said psychotic disorder is a schizophrenic disorder.

8. The method of claim 7 wherein said schizophrenic disorder is a PCP-induced schizophrenic disorder.

* * * * *